United States Patent [19]

Seltzer et al.

[11] Patent Number: 4,847,367

[45] Date of Patent: Jul. 11, 1989

[54] 4-HIGHER ALKYL-2-NITRO-2'-HYDROXY-3',5'-DI-HIGHER ALKYL (OR CUMYL)-AZOBENZENES

[75] Inventors: Raymond Seltzer, New City; Roland A. E. Winter, Armonk, both of N.Y.

[73] Assignee: Ciba-Geigy Corporation, Ardsley, N.Y.

[21] Appl. No.: 120,441

[22] Filed: Nov. 13, 1987

Related U.S. Application Data

[62] Division of Ser. No. 772,222, Sep. 3, 1985, Pat. No. 4,727,158.

[51] Int. Cl.$^4$ .................. C07C 107/06; C09B 29/01; C09B 29/12
[52] U.S. Cl. .................. 534/649; 534/558; 534/565
[58] Field of Search .................. 534/649, 683

[56] References Cited

U.S. PATENT DOCUMENTS

| | | | |
|---|---|---|---|
| 3,998,804 | 12/1976 | Rody et al. | 534/649 X |
| 4,226,763 | 10/1980 | Dexter et al. | 548/260 X |
| 4,275,004 | 6/1981 | Winter et al. | 534/649 X |
| 4,278,589 | 7/1981 | Dexter et al. | 548/260 X |
| 4,347,180 | 8/1982 | Winter et al. | 534/649 X |

FOREIGN PATENT DOCUMENTS

| | | | |
|---|---|---|---|
| 1358128 | 3/1964 | France | 534/649 |
| 55-94348 | 7/1980 | Japan | 534/649 |

OTHER PUBLICATIONS

Tanimoto et al., J. Synthetic Org. Chem., vol. of 1986, pp. 647–649.

*Primary Examiner*—Floyd D. Higel
*Attorney, Agent, or Firm*—Luther A. R. Hall

[57] ABSTRACT

4-Higher alkyl-2-nitro-2'-hydroxy-3',5'-di-higher alkyl (or cumyl)-azobenzenes are made by coupling the corresponding diazotized 4-higher alkyl-o-nitroaniline with the corresponding substituted phenol. These azobenzene intermediates are used to prepare the corresponding 2H-benzotriazole UV absorber stabilizers substituted on the 5-position of the benzo ring by a higher alkyl group, preferably tert-octyl or n-dodecyl.

3 Claims, No Drawings

4-HIGHER ALKYL-2-NITRO-2'-HYDROXY-3',5'-DI-HIGHER ALKYL (OR CUMYL)-AZOBENZENES

This is a divisional of application Ser. No. 772,222 filed on Sept. 3, 1985, now U.S. Pat. No. 4,727,158, issued on Feb. 23, 1988.

BACKGROUND OF THE INVENTION

The present invention relates to selected 2-aryl-2H-benzotriazoles which are useful in protetting light-sensitive organic materials from deterioration and to stabilized compositions containing said benzotriazoles.

The UV absorbers of the o-hydroxyphenyl-2H-benzotriazole class have long been known as effective light stabilizers for organic materials and have enjoyed considerable commercial success.

However, the hitherto known 2-aryl-2H-benzotriazoles of this group have in some circumstances exhibited limited compatibility in certain substrates, and excessive tendency to exude, sublime and/or volatilize during processing of stabilized compositions into sheets, films, fibers or other pellicles when processing must be done at elevated temperatures. Likewise such benzotriazoles may also suffer undue loss by volatilization or sublimation from fabricated structures, particularly thin films or coatings, especially when subjected to elevated temperatures during use.

Attempts have been made to increase substrate compatibility or solubility and to reduce volatilization loss by modifying the structure of the benzotriazoles.

In U.S. Pat. No. 3,230,194, a higher alkyl group was substituted for methyl and the compound 2-(2-hydroxy-5-tert-octylphenyl)-2H-benzotriazole exhibited superior compatibility and performance in polyethylene.

In U.S. Pat. No. 4,127,586, still other modifications to the 2-aryl-2H-benzotriazole moiety were made to increase still further compatibility in substrates and resistance to volatilization. The compound 2-[2-hydroxy-3-(1-phenylethyl)-5-methylphenyl]-2H-benzotriazole described therein exhibited better compatibility and better resistance to loss by volatilization during processing than did the earlier prior art benzotriazole compounds.

In Japanese Kokai No. 158588/75, other benzotriazole light stabilizers such as 2-(2-hydroxy-3-alpha,alpha-dimethylbenzyl-5-methylphenyl)-2H-benzotriazole are disclosed.

However, still better resistance to loss from stabilized compositions during high temperature processing remained a practical objective and need in the art for the benzotriazole UV-absorbers.

U.S. Pat. No. 4,226,763 describes attempts to increase the resistance of benzotriazole light absorbers to loss by volatilization. This patent describes 2-(2-hydroxy-3,5-di-alpha-cumylphenyl)-2H-benzotriazole which exhibits superior resistance to loss from stabilized compositions during high temperature processing or in end use applications where coatings or films of the stabilized compositions are exposed even to ambient weathering and light exposures compared to stabilized compositions containing the 2-aryl-2H-benzotriazoles of the prior art. This superior performance is attained at the cost of relatively low solubility in some substrates and processing solvents.

U.S. Pat. No. 4,283,327 describes 2-(2-hydroxy-3,5-di-tert-octylphenyl)-2H-benzotriazole which exhibits enhanced solubility in processing solvents and substrates, but which did not have outstanding resistance to loss by volatilization.

U.S. Pat. No. 4,278,589 describes benzotriazoles having one alpha-cumyl group and one tert-octyl substituent on the 2-phenyl moiety in an attempt to achieve a balance of properties not obtained with two alpha-cumyl or with two tert-octyl groups. Benzotriazoles with a good balance of solubility and resistance to loss by volatilization were obtained, but not the outstanding levels of each required by an increasingly demanding market place for light stabilizers with truly exceptional properties.

Although lower alkyl, and halogen substitution on the benzo ring of 2H-benzotriazoles has long been known for example in U.S. Pat. No. 4,127,586 and Japanese Sho No. 59/172,655, the substitution of the benzo ring with higher alkyl, groups is not known.

Traditionally lacquers have been used in the automotive and other industries to produce high gloss coatings. Such lacquers typically consist of high molecular weight polymers dissolved in appropriate solvents. The solvents which usually constitute over 70% of the paint evaporate on baking to leave a polymer film.

Energy and environmental considerations have more recently resulted in development of so called "high solids enamels" as alternate coating systems, which meet government mandated reduction in "volatile organic compounds (VOC)". High solids enamels typically consist of low molecular weight copolymers of methyl methacrylate, hydroxyethyl methacrylate, butyl acrylate and styrene. Such copolymers which contain pendant hydroxyl groups are then blended with melamine crosslinking resins (ratios of about 7:3). The final crosslinking reaction occurs when the painted article is subjected to baking. High solids enamels in contrast to lacquers contain usually less than 50% solvent.

The bulk of these solvents are employed during the monomer polymerization process. Only a small quantity of solvents generally less than 10% of the total solvent is retained as "hold out" solvent to be added later to the final paint. The light stabilizing additives must be soluble enough in this hold out solvent to permit incorporation at this stage. The amount of solvent cannot be changed at will because paint viscosity is a critical parameter in avoiding defects such as runs and sags. To meet these demands for high solubility the instant stabilizers were developed. These products also meet and/or exceed the state of the art materials with respect to compability with the resin and lack of volatility.

DETAILED DISCLOSURE

This invention pertains to selected 2-aryl-2H-benzotriazole light absorbers and to organic materials stabilized thereby.

More particularly, the 2-aryl-2H-benzotriazoles of this invention are represented by the formula I

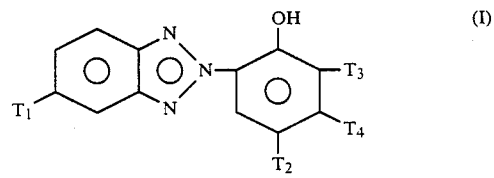

wherein
  $T_1$ is alkyl of 8 to 18 carbon atoms, and $T_2$ and $T_3$ are independently hydrogen, hydroxyl, alkyl of 8 to 18 carbon atoms or a group of formula II

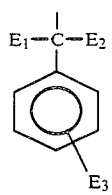
(II)

wherein $E_1$ and $E_2$ are independently hydrogen or alkyl of 1 to 4 carbon atoms and $E_3$ is hydrogen, halogen or alkyl of 1 to 4 carbon atoms, $T_4$ is hydrogen or hydroxyl, with the proviso that $T_2$, $T_3$ and $T_4$ cannot each be hydrogen at the same time, and that only one of $T_2$, $T_3$ and $T_4$ can be hydroxyl at the same time.

When $T_1$, $T_2$ or $T_3$ is alkyl of 8 to 18 carbon atoms, it may be for example 2-ethylhexyl, n-octyl, tert-octyl, n-dodecyl, tert-dodecyl or n-octadecyl.

When $E_1$, $E_2$ or $E_3$ is alkyl of 1 to 4 carbon atoms, it is for example methyl, ethyl, n-propyl, isopropyl, n-butyl or tert-butyl.

When $E_3$ is halogen, it may be fluorine, bromine, chlorine or iodine, preferably chlorine.

Preferably $T_1$ is alkyl of 8 to 12 carbon atoms.

Preferably $T_2$ and $T_3$ are independently alkyl of 8 to 12 carbon atoms, most preferably tert-octyl, or a group of formula II where $E_1$ and $E_2$ are each methyl and $E_3$ is hydrogen or p-methyl, most preferably alpha,alpha-dimethylbenzyl.

Preferably $T_4$ is hydrogen.

SYNTHESIS OF COMPOUNDS

The compounds of this invention are prepared the manner set forth in U.S. Pat. No. 4,226,763 wherein the substituted 2-nitroaniline is diazotized and then coupled, preferably in a strongly alkaline medium, with the appropriate phenol to give the intermediate o-nitroazobenzene.

This o-nitroazobenzene intermediate is converted to the corresponding 2-aryl-2H-benzotriazole by reductive cyclization using any number of conventional reducing systems including zinc and alkali, hydrazine, catalytic hydrogenation, and the like.

Many of the various starting materials such as the substituted phenols, o-nitroaniline, alpha-methylstyrene, styrene, benzyl alcohol, and the like are items of commerce or can easily be prepared by known methods.

The substituted phenols are conveniently made by the alkylation of phenol with an olefin in the presence of an acidic catalyst. The preparation of 2,4-di(alpha,alpha-dimethylbenzyl)phenol, described in U.S. Pat. No. 4,226,763, is a typical illustration.

The substituted o-nitroanilines required to obtain the instant compounds substituted on the 5-position of the benzo ring with higher alkyl groups can be prepared by the direct alkylation of o-nitroaniline with an olefin such as diisobutylene in the presence of an acidic catalyst or from an alkylated aniline, such as 4-n-dodecylaniline, by acetylation of the amino group, followed by nitration and finally by hydrolysis to remove the protecting acetyl group from the amine.

The o-nitroazobenzene intermediates of formula III

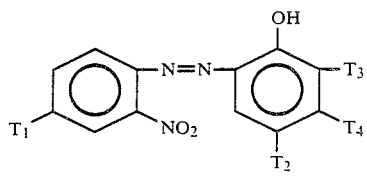
(III)

where $T_1$, $T_2$, $T_3$ and $T_4$ are defined above are also new compounds and are part of this invention.

The compounds of this invention are effective light stabilizers in a wide range of organic polymers. Polymers which can be stabilized include:

1. Polymers which are derived from mono- or diolefins, e.g., polyethylene which can optionally be cross-linked, polypropylene, polyisobutylene, polymethylbutene-1, polymethylpen-tene-1, polyisoprene, polybutadiene.

2. Mixtures of the homopolymers cited under (1) for example mixtures of polypropylene and polyethylene, polypropylene and polybutene-1, polypropylene and polyisobutylene.

3. Copolymers of the monomers based on the homopolymers cited under (1), for example ethylene/propylene copolymers, propylene/butene-1 copolymers, propylene/isobutylene copolymers, ethylene/butene-1 copolymers as well as terpolymers of ethylene and propylene with a diene, for example hexadiene, dicyclopentadiene or ethylidene norbornene, and copolymers of α-olefins, e.g., ethylene with acrylic or methacrylic acid.

4. Polystyrene.

5. Copolymers of styrene and of α-methylstyrene, for example styrene/butadiene copolymers, styrene/acrylonitrile copolymers, styrene/acrylonitrile/methacrylate copolymers, styrene/acrylonitrile copolymers modified with acrylic ester polymers to provide impact strength as well as block copolymers, e.g., styrene/butadiene/styrene block copolymers.

6. Graft copolymers of styrene, for example the graft polymer of styrene to polybutadiene, the graft polymer of styrene with acrylonitrile to polybutadiene as well as mixtures thereof with the copolymers cited under (5), commonly referred to as acrylonitrile/butadiene/styrene or ABS plastics.

7. Halogen-containing vinyl polymers, for example polyvinyl chloride, polyvinylidene chloride, polyvinyl fluoride, polychloroprene, chlorinated rubbers, vinyl chloride/vinylidene chloride copolymers, vinyl chloride/vinyl acetate copolymers, vinylidene chloride/vinyl acetate copolymers.

8. Polymers which are derived from α,β-unsaturated acids and derivatives thereof, polyacrylates and polymethacrylates, polyacrylic amides and polyacrylonitrile. The instant compounds are advantageously used in heat-curable acrylic resin lacquers which are composed of a copolymer of acrylic acid and one or more of its derivatives, and a melamine-formaldehyde resin.

9. Polymers which are derived from unsaturated alcohols and amines and from the acyl derivatives thereof or acetals, for example polyvinyl alcohol, polyvinyl acetate, polyvinyl stearate, polyvinyl benzoate, polyvinyl maleate, polyvinyl butyral, polyallyl phthalate, polyallyl melamine and copolymers thereof with other vinyl compounds, for example ethylene/vinyl acetate copolymers.

10. Homopolymers and copolymers which are derived from epoxides, for example polyethylene oxide or the polymers which are derived from bis-glycidyl ethers.

11. Polyacetals, for example polyoxymethylene, as well as polyoxymethylenes which contain ethylene oxide as comonomer.

12. Polyalkylene oxides, for example polyoxyethylene, polypropylene oxide or polyisobutylene oxide.

13. Polyphenylene oxides.

14. Polyurethanes and polyureas, such as in urethane coatings.

15. Polycarbonates.

16. Polysulfones.

17. Polyamides and copolyamides which are derived from diamines and dicarboxylic acids and/or from aminocarboxylic acids or the corresponding lactams, for example polyamide 6, polyamide 6/6, polyamide 6/10, polyamide 11, polyamide 12, poly-m-phenylene-isophthalamide.

18. Polyesters which are derived from dicarboxylic acids and dialcohols and/or from hydroxycarboxylic acids or the corresponding lactones, for example polyethylene glycol terephthalate, poly-1,4-dimethylolcyclohexane terephthalate.

19. Cross-linked polymers which are derived from aldehydes on the one hand and from phenols, ureas and melamine on the other, for example phenol/formaldehyde, urea/formaldehyde and melamine/formaldehyde resins.

20. Alkyd resins, for example glycerol/phthalic acid resins and mixtures thereof with melamine/formaldehyde resins.

21. Unsaturated polyesters resins which are derived from copolyesters of saturated and unsaturated dicarboxylic acids with polyhydric alcohols as well as from vinyl compounds as cross-linking agents and also the halogen-containing, flame-resistant modifications thereof.

22. Natural polymers, for example cellulose, rubber, as well as the chemically modified homologous derivatives thereof, for example cellulose acetates, cellulose propionates and cellulose butyrates and the cellulose ethers, for example methyl cellulose.

While compounds of this invention are very effective stabilizers for a host of organic substrates subject to light induced deterioration, as are the 2-aryl-2H-benzotriazole light absorbers in general, the instant compounds with their surprising resistance to loss from a stabilized composition during high temperature processing due to volatilization, exudation or sublimation have particular value in stabilizing polymeric substrates which are perforce processed at elevated temperatures.

Thus, the compounds of this invention are particularly useful as stabilizers for the protection of polyesters, for instance poly(ethylene terephthalate), poly(butylene terephthalate) or copolymers thereof; of polycarbonates, for example polycarbonate derived from bisphenol A and phosgene, or copolymers thereof; of polsulfones; of polyamides such as nylon-6, nylon-6,6, nylon 6,10 and the like as well as copolyamides; of thermoset acrylic resins; of thermoplastic acrylic resins; of polyolefins such as polyethylene, polypropylene, copolyolefins and the like; and of any polymer system requiring high temperature processing and fabrication.

Although the compounds of the invention may be used above to provide a light stabilizing function, the compounds of this invention are often combined with other stabilizers, even other light stabilizers, in the preparation of stabilized compositions. The stabilizers may be used with phenolic antioxidants, pigments, colorants or dyes, light stabilizers such as hindered amines, metal deactivators, etc.

In general, the stabilizers of this invention are employed from about 0.1 to about 5% by weight of the stabilized composition, although this will vary with the particular substrate and application. An advantageous range is from about 0.5 to about 3%.

The stabilizers of Formula I may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The stabilized polymer compositions of the invention may optionally also contain from about 0.1 to about 5%, preferably from about 0.5 to about 3% by weight of various conventional additives, such as the following, particularly phenolic antioxidants or light-stabilizers, or mixtures thereof:

1. Antioxidants 1.1 Simple 2,6-dialkylphenols, such as, for example, 2,6-di-tert.-butyl-4-methylphenol, 2-tert.-butyl-4,6-dimethylphenol, 2,6-di-tert.-butyl-4-methoxymethylphenol and 2,6-dioctadecyl-4-methylphenol.

1.2 Derivatives of alkylated hydroquinones, such as for example, 2,5-di-tert.-butyl-hydroquinone, 2,5-di-tert.-amylhydroquinone, 2,6-di-tert.- butyl hydroquinone, 2,5-di-tert.-butyl-4-hydroxy-anisole, 3,5-di-tert.-butyl-4-hydroxy-anisole, 3,5-di-tert.-butyl-4-hydroxyphenyl stearate and bis-(3,5-di-tert.-butyl-4-hydroxyphenyl) adipate.

1.3 Hydroxylated thiodiphenyl ethers, such as for example, 2,2'-thio-bis-(6-tert.-butyl-4-methylphenol), 2,2'-thio-bis-(4-octylphenol), 4,4'-thio-bis-(6-tert.-butyl-3-methylphenol), 4,4-thio-bis-(3,6-di-sec.-amylphenol), 4,4'-thio-bis-(6-tert.-butyl-2-methylphenol) and 4,4'-bis-(2,6-dimethyl-4-hydroxyphenyl) disulfide.

1.4 Alkylidene-bisphenols, such as, for example, 2,2'-methylene-bis-(6-tert.-butyl-4-methylphenol), 2,2'-methylene-bis-(6-tert.-butyl-4-ethylphenol), 4,4'-methylene-bis-(6-tert.-butyl-2-methylphenol, 4,4'-methylene-bis-(2,6-di-tert.-butylphenol), 2,6-di(3-tert.-butyl-5-methyl-2-hydroxybenzyl)- 4-methylphenol, 2,2'-methylene-bis-[4-methyl-6-(α-methylcyclohexyl)-phenol], 1,1-bis(3,5-dimethyl-2-hydroxyphenyl)-butane, 1,1-bis-(5-tert.-butyl-4-hydroxy-2-methylphenyl)-butane, 2,2-bis-(3,5-di-tert.-butyl-4-hydroxyphenyl)-propane, 1,1,3-tris-(5-tert.-butyl-4-hydroxy-2-methylphenyl)-butane, 2,2-bis-(5-tert.-butyl-4-hydroxy-2-methylphenyl)-4-n-dodecylmercaptobutane, 1,1,5,5-tetra-(5-tert.-butyl-4-hydroxy-2-methylphenyl)pentane and ethylene glycol bis-[3,3-bis -(3-tert.-butyl-4-hydroxyphenyl)-butyrate].

1.5 O-, N- and S-benzyl compounds, such as for example, 3,5,3',5'-tetra-tert.-butyl-4,4'-dihydroxydibenzyl ether, octadecyl 4-hydroxy-3,5-dimethylbenzyl mercaptoacetate, tris-(3,5-di-tert.-butyl-4-hydroxybenzyl)-amine and bis-(4-tert.-butyl-3-hydroxy-2,6-dimethylbenzyl) dithioterephthalate.

1.6 Hydroxybenzylated malonates, such as for example, dioctadecyl 2,2-bis-(3,5-di-tert.-butyl-2-hydroxybenzyl)-malonate, dioctadecyl 2-(3-tert.-butyl-4-hydroxy-5-methylbenzyl)-malonate, di-dodecylmercapto-ethyl 2,2-bis-(3,5-di-tert.-butyl-4-hydroxybenzyl)- malonate and di-[4-(1,1,3,3-tetramethylbutyl)phenyl] 2,2-bis-(3,5-di-tert.-butyl-4-hydroxybenzyl)-malonate.

1.7 Hydroxybenzyl-aromatic compounds, such as, for example, 1,3,5-tri-(3,5-di-tert.-butyl-4-hydroxybenzyl)-2,4,6-trimethylbenzene, 1,4-di-(3,5-di-tert-butyl-4-hydroxybenzyl)-2,3,5,6-tetramethylbenzene and 2,4,6-tri-(3,5-di-tert.-butyl-4-hydroxybenzyl)-phenol.

1.8 s-Triazine compounds, such as, for example 2,4-bis-octylmercapto-6-(3,5-di-tert.-butyl-4-hydroxyanilino)-s-triazine, 2-octylmercapto-4,6-bis-(3,5-di-tert.butyl-4-hydroxy anilino)-s-triazine, 2-octylmercapto-4,6-bis-(3,5-di-tert.-butyl-4-hydroxyphenoxy)-s-triazine, 2,4,6-tris-(3,5-di-tert-butyl-4-hydroxyphenoxy)-s-triazine, 2,4,6-tris-(3,5-di-tert-butyl-4-hydroxyphenylethyl)-s-triazine and 1,3,5-tris-(3,5-di-tert.-butyl-4-hydroxybenzyl)isocyanurate.

1.9 Amides of β-(3,5-di-tert.-butyl-4-hydroxyphenyl)-propionic acid, such as, for example, 1,3,5-tris-(3,5,di-tert.-butyl-4-hydroxyphenyl-propionyl)-hexahydro-s-triazine and N,N'-di-3,5-di-tert.-butyl-4-Hydroxyphenyl-propionyl)-hexameth -ylenediamine, N,N'-bis-β-(3,5 di-t-butyl-4-hydroxyphenyl)-propionyl-hydrazine.

1.10 Esters of β-(3,5-di-tert.-butyl-4-hydroxyphenyl)-propionic acid with monohydric or polyhydric alcohols, such as for example, with methanol, ethanol, octadecanol, 1,6-hexanediol, 1,9-nonanediol, ethylene glycol, 1,2-propanediol, diethylene glycol, thiodiethylene glycol, neopentylglycol, pentaerythritol, 3-thiaundecanol, 3-thia-pentadecanol, trimethylhexnediol, trimethylolethane, trimethylolpropane, tris-hydroxyethyl isocyanurate and 4-hydroxymethyl-1-phospha-2,6,7-trioxabicyclo-[2.2.2]octane.

1.11 Esters of β-(5-tert.-butyl-4-hydroxy-3-methylphenylpropionic acid with monohydric or polyhydric alcohols, such as for example, with methanol, ethanol, octadecanol, 1,6-hexanediol, 1,9-nonanediol, ethylene glycol, 1,2-propanediol, diethylene glycol, thiodiethylene glycol, neopentylglycol, pentaerythritol, 3-thiaundecanol, 3-thia-pentadecanol, trimethylhexanediol, trimethylolethane, trimethylolpropane, tris-hydroxyethyl isocyanurate and 4-hydroxymethyl-1-phospha-2,6,7-trioxabicyclo[2.2.2]octane.

1.12 Esters of 3,5-di-tert.-butyl-4-hydroxyphenylacetic acid with monohydric or polyhydric alcohols, such as for example, with methanol, ethanol, octadecanol, 1,6-hexandiol, 1,9-nonanediol, ethylene glycol, 1,2-propenediol, diethylene glycol, thio-diethylene glycol, neopentylglycol, pentaerythritol, 3-thia-undecanol, 3-thia-pentadecanol, trimethylhexanediol, trimethylolethane, trimethylolpropane, tris-hydroxyethyl isocyanurate and 4-hydroxymethyl-1-phospha-2,6,7-trioxabicyclo[2.2.2]-octane especially the tetrakis ester of pentaerythritol.

1.13 Benzylphosphonates, such as, for example, dimethyl 3,5-di-tert.-butyl-4-hydroxybenzylphosphonate, diethyl 3,5-di-tert.-butyl-4-hydroxybenzylphosphonate, dioctadecyl 3,5-di-tert.-butyl-4-hydroxybenzylphosphonate and dioctadecyl 5-tert.-butyl-4-hydroxy-3-methylbenzylphosphonate.

2. Light-stabilizers 2.1 Esters of optionally substituted benzoic acids, e.g., 3,5-di-tert.-butyl-4-hydroxybenzoic acid, 2,4-di-tert.-butylphenyl ester or -octadecyl ester or 2-methyl-4,6-di-tert.-butylphenyl ester.

2.2 Sterically hindered amines, e.g., 4-benzoyl-2,2,6,6-tetramethylpiperidine, 4-stearyloxy-2,2,6,6-tetramethylpiperidine, bis-(2,2,6,6-tetramethylpiperidyl) sebacate, bis-(1,2,2,6,6-pentamethylpiperidyl) 2-n-butyl-2-(2-hydroxy-3,5-di-tert-butylbenzyl)malonate or 3-n-octyl-7,7,9,9-trimethyl-1,3,8-triazaspiro[4.5]decane-2,4-dione.

2.3 Oxalic acid diamides, e.g., 4,4'-di-octyloxy-oxanilide, 2,2'-di-octyloxy-5,5'-di-tert.-butyl oxanilide, 2,2'-di-dodecyloxy-5,5'-di-tert.-butyl-oxanilide, 2-ethoxy-2'-ethyl-oxanilide, N,N'bis(3-dimethyl aminopropyl)-oxalamide, 2ethoxy-5-tert.-butyl-2'-ethyl-oxanilide and the mixture thereof with 2-ethoxy-2'-ethyl-5,4'-di-tert.-butyl-oxanilide, or mixtures of ortho- and para-methoxy- as well as of o- and p-ethoxy-disubstituted oxanilides.

3. Metal deactivators, e.g., oxanilide, isophthalic acid dihydrazide, sebacic acid-bis-phenylhydrazide, bis-benzylideneoxalic acid dihydrazide, N,N'-diacetal-adipic acid dihydrazide, N,N'-bis-salicyloyl-oxalic acid dihydrazide, N,N'-bis-salicyloylhydrazine, N,N'-bis-(3,5-di-tert.-butyl-4-hydroxyphenylpropionyl)-hydrazine, N-salicyloyl-N'-salicylalhydrazine, 3-salicyloyl-amino-1,2-4-triazole or N,N'-bis-salicyloyl-thiopropionic acid dihydrazide.

4. Basic co-stabilizers, e.g., alkali metal salts and alkaline-earth metal salts of higher fatty acids, for example Ca-stearate, Zn-stearate, Mg-behenate, Na-ricinoleate or K-palmitate.

5. Nucleation agents, e.g., 4-tert.-butylbenzoic acid, adipic acid or diphenylacetic acid.

6. Phosphites and phosphonites, such as, for example, triphenyl phosphite, diphenylalkyl phosphites, phenyldialkyl phosphites, tri-(nonyl-phenyl) phosphite, trilauryl phosphite, trioctadecyl phosphite and 3,9-isodecyloxy-2,4,8,10-tetraoxa-3,9-diphospha-[5.5]-undecane and tetra(2,4-di-tert-butylphenyl) diphenylene-4,4'-bis(phosphonite).

Other additives that can be incorporated in the stabilized compositions are thiosynergists such as dilauryl thiodipropionate, lubricants such as stearyl alcohol, fillers, asbestos, kaolin, talc, glass fibers, pigments, optical brighteners, flameproofing agents and antistatic agents.

The following examples are presented for the purpose of illustration only and are not to be construed to limit the nature or scope of the instant invention in any manner whatsoever.

EXAMPLE 1

4-tert-Octyl-2-nitroaniline

In a 2-liter reaction flask fitted with a condenser, nitrogen inlet, stirrer, thermometer and addition funnel is placed 272 grams (2.0 moles) of anhydrous zinc chloride. The flask is placed under a nitrogen atmosphere and 166 ml (2.0 moles) of concentrated (12N) hydrochloric acid is added over a 10-minute period with the temperature rising from 22° to 40° C. To this is then added 276 grams (2.0 moles) of o-nitroaniline over a 15-minute period to avoid the formation of lumps. The resulting thick red slurry is heated to 60° C. and then 474 grams (3.0 moles) of diisobutylene is added gradually over a 110-minute period with the temperature rising during this period from 60° to 90° C. The deep red fluid reaction mixture is heated for another 18 hours at reflux till only a trace of o-nitroaniline is observed by thin layer chromatography.

The crude product is a solid which is triturated twice with water and then dissolved in warm toluene. The toluene phase is separated from the lower aqueous layer and is then dried over anhydrous potassium carbonate.

The toluene is removed in vacuo to give a solid which is recrystallized once from ethylene glycol and then again from heptane to give the above-named product in a yield of 77.2 grams (15.6%) as a solid melting at 104°–107° C. The product is of high pruity giving only one spot in thin layer chromatography.

EXAMPLE 2 a. N-Acetyl-4-n-dodecylaniline

In a 1-liter flask fitted with a stirrer and reflux condenser is added 137.5 grams (0.525 mole) of p-n-dodecylaniline, dissolved in 138 ml of toluene. To this is added over a 15-minute period 57.5 ml of acetic anhydride. The temperature rises from 40° to 80° C. After all the acetic anhydride is added, the reaction mixture is stirred at 40° C. for 3 hours. The reaction mixture is then cooled to yield the crude product which is recrystallized from 800 ml of methanol to give 151.1 grams of the above-named material as a solid melting at 100°–102° C.

b. N-Acetyl-4-n-dodecyl-2-nitroaniline

To a 2-liter round-bottom flask fitted with a stirrer is added 146 grams of N-acetyl-4-n-dodecylaniline, prepared in Example 2a, dissolved in 150 ml of glacial acetic acid. To this is added 300 ml of concentrated sulfuric acid with the temperature rising to 62° C. To this solution is now added dropwise over an hour period a solution of 66 ml of concentrated (70%) nitric acid and 42 ml of concentrated sulfuric acid, keeping the reaction mixture at 55° C. by external cooling. After the exotherm subsides, the reaction mixture is heated to 45° C. with the overall reaction time being four hours. The reaction mixture is poured onto 4 liters of ice and the solid product is isolated by filtration. The crude product is recrystallized several times from petroleum ether to give 55.6 grams of pure product melting at 71°–73° C.

c. 4-n-Dodecyl-2-nitroaniline

In a 1-liter flask fitted with a stirrer and reflux condenser, 61.8 grams of N-acetyl-4-n-dodecyl-2-nitroaniline (prepared in Example 2b), 320 ml of ethanol and 64 ml of 40% aqueous potassium hydroxide solution are heated for 1 hour under reflux. The reaction mixture is cooled and then poured into 1.5 liters of water. The crude product is isolated by filtration, washed repeatedly with cold water and recrystallized from methanol. The above-named product is isolated as a solid melting at 69°–71° C. in a yield of 45 grams.

Analysis: Calcd for $C_{18}H_{30}N_2O_2$: C, 70.54; H, 9.86; N, 9.14. Found: C, 70.5; H, 9.7; N, 9.1.

EXAMPLE 3

2,4-Di-(alpha,alpha-dimethylbenzyl)phenol

This intermediate is made by reacting a mixture of 705.8 grams (7.5 moles) of phenol with 1772.7 grams (15 moles) of alpha-methylstyrene in the presence of 25.7 grams (0.135 moles) of p-toluenesulfonic acid monohydrate catalyst. This mixture is heated under nitrogen at 140° C. for 2.5 hours. The reaction mixture is cooled to 110° C. and 1125 ml of toluene is added. After washing the resulting solution at 80° C. with 750 ml of an aqueous solution of 37.5 grams of sodium carbonate and 75 grams of sodium chloride, the organic phase is washed thrice with 1000 ml of aqueous sodium chloride solution; then dried over anhydrous sodium sulfate; filtered and vacuum distilled. The above-named product is obtained as the main fraction boiling at 172°–175° C./0.15–0.18 mm Hg in a yield of 1229.8 grams (49.6% of theory). The product melts at 63°–65° C.

EXAMPLE 4

4-tert-Octyl-2-nitrobenzene Diazonium Chloride

In a 100-ml flask fitted with a stirrer and thermometer, 15.0 grams (0.06 mole) of 4-tert-octyl-2-nitroaniline is suspended in 20 ml of toluene. To this is added at 25° C. 17.3 grams (0.18 mole) of concentrated hydrochloric acid. The suspension is stirred at 38° C. for 1 hour followed by the addition of 6 ml of water. The mixture becomes thick as the corresponding hydrochloride salt crystallized as a granular precipitate. The mixture is cooled to 0° C. and diazotized by the addition over a period of 30 minutes of 4.3 grams (0.062 mole) of sodium nitrite in 6 ml of water keeping the temperature at −5° C. to −2° C. The mixture is stirred at −2° C. for 1 hour. Two phases occur. The combined phases contain the desired diazonium chloride and are used as is.

EXAMPLE 5

4-tert-Octyl-2-nitro-2'-hydroxy-3',5'-di-(alpha,alpha-dimethylbenzyl)azobenzene In a 500 ml flask, 13.6 grams (0.34 moles) of sodium hydroxide pellets are dissolved in 165 ml of methanol. To this is added 16.5 grams (0.05 mole) of 2,4-di-(alpha,alpha-dimethylbenzyl)phenol and 20 ml of toluene. The resulting solution is cooled to 0° C. Over a period of 6 hours is added the diazonium chloride solution (0.06 mole), prepared in Example 4, keeping the temperature at 0° C. Heptane (20 ml) is added to achieve better mobility. After stirring for 2 hours, the pH of the reaction mixture is brought to 9 by the addition of 15 ml of acetic acid.

Water is added to separate the phases. The product is in the upper organic phase which is diluted with heptane, washed with water, dried over anhydrous sodium sulfate and stripped in vacuo to give the above-named product in essentially quantitative yield.

EXAMPLE 6

5-tert-Octyl-2-[2-hydroxy-3,5-di-(alpha,alpha-dimethylbenzyl)phenyl]-2H-benzotriazole To a 300 ml 3-necked flask fitted with a stirrer, thermometer, reflux condenser and nitrogen inlet is charged 31 grams (0.05 mol) of the o-nitroazobenzene intermediate of Example 5 and 100 ml of toluene. To the resulting solution is added 15 ml of isopropanol and 15 ml of water. A nitrogen atmosphere is imposed and 8 grams (0.1 mole) of 50% aqueous sodium hydroxide is added. A flask containing 11.6 grams (0.177 gram-atoms) of zinc is connected to the reaction flask by Gooch rubber tubing and the zinc dust is added portionwise to the reaction mixture in essentially eight (8) equal portions with 15 minute intervals between additions. After all the zinc is added, the mixture is stirred at 47° C. overnight and then heated to reflux for two hours. The mixture is then cooled to 45° C. and acidified with 50 grams of 50% aqueous sulfuric acid.

The zinc sludge is removed by filtration. The product is contained in the organic layer, which is washed with three 20 ml portions of 70% sulfuric acid, and with four 20 ml portions of 88% formic acid, with water, with brine and then dried over anhydrous sodium sulfate. The toluene solution is condentrated to 30 grams and then diluted with 85 ml of isopropanol. The above-named product is obtained in a yield of 13.6 grams (48.6%) as a white solid melting at 140°–142° C.

Analysis: Calcd for $C_{38}H_{45}N_3O$: C, 81.53; H, 8.10; N, 7.51. Found: C, 81.6; H, 7.8; N, 7.4.

EXAMPLE 7

4-n-Dodecyl-2-nitrobenzene Diazonium Chloride

When following the general procedure of Example 4 an equivalent amount of 4-n-dodecyl-2-nitroaniline is substituted for the 4-tert-octyl-2-nitroaniline, the above-named diazonium chloride solution is obtained.

EXAMPLES 8–14 o-Nitroazobenzene Intermediates

Using the general procedure of Example 6, the following o-nitroazobenzene intermediates are prepared by selecting the appropriate diazonium chloride solution and the appropriate phenol.

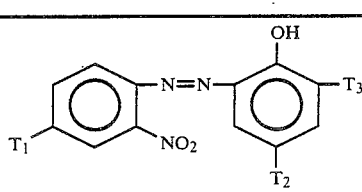

| Example | $T_1$ | $T_2$ | $T_3$ |
|---------|-------|-------|-------|
| 8  | tert-octyl*  | tert-octyl   | alpha-cumyl |
| 9  | tert-octyl*  | alpha-cumyl  | tert-octyl  |
| 10 | tert-octyl*  | tert-octyl   | tert-octyl  |
| 11 | n-dodecyl**  | alpha-cumyl  | alpha-cumyl |
| 12 | n-dodecyl**  | tert-octyl   | alpha-cumyl |
| 13 | n-dodecyl**  | alpha-cumyl  | tert-octyl  |
| 14 | n-dodecyl**  | tert-octyl   | tert-octyl  |

*from diazonium chloride of Example 4
**from diazonium chloride of Example 7

EXAMPLE 15

5-n-Dodecyl-2-[2-hydroxy-3,5-di-(alpha,alpha-dimethylbenzyl)phenyl]-2H-benzotriazole Using the general procedure of Example 6 and the o-nitroazobenzene intermediate of Example 11, the above-named product is obtained in a yield of 72% as a non-crystalline solid.

Analysis: Calcd for $C_{42}H_{53}N_3O$: C, 81.90; H, 8.68; N, 6.82. Found: C, 82.0; H, 9.0; N, 6.5.

EXAMPLES 16–21

Using the general procedure of Example 6 and the appropriate o-nitroazobenzene intermediates of Examples 8–10 and 12–14, the following 2H-benzotriazoles are prepared.

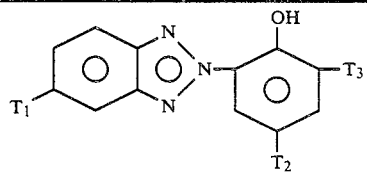

| Example | $T_1$ | $T_2$ | $T_3$ |
|---------|-------|-------|-------|
| 16 | tert-octyl | tert-octyl  | alpha-cumyl |
| 17 | tert-octyl | alpha-cumyl | tert-octyl  |
| 18 | tert-octyl | tert-octyl  | tert-octyl  |
| 19 | n-dodecyl  | tert-octyl  | alpha-cumyl |

-continued

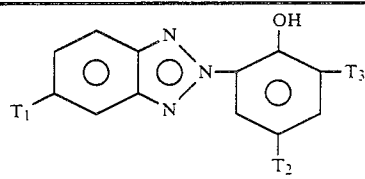

| Example | $T_1$ | $T_2$ | $T_3$ |
|---------|-------|-------|-------|
| 20 | n-dodecyl | alpha-cumyl | tert-octyl |
| 21 | n-dodecyl | tert-octyl  | tert-octyl |

EXAMPLE 22

Resistance to Loss of Benzotriazole Stabilizers

A number of 2-aryl-2H-benzotriazole light stabilizers are subjected to thermal gravimetric analysis with a flow rate of 100 m nitrogen/minute both isothermally at 280° C. to indicate the time in minutes to reach 50% weight loss of the stabilizer as well as in a scanning mode at a heating rate of 10° (C.) per minute to ascertain the temperature at which 10% and 50% weight loss of stabilizer are observed.

Experimental data are given on the table which follows.

These results correlate closely with the resistance of the indicated stabilizer to exudation or volatilization during any processing step with polymer formulations during the preparation of sheet, film, fiber or other fabricated pellicles. The absence or essential absence of exuded or volatilized stabilizer on processing equipment (i.e., rollers, guides, orifices, and the like) increases significantly the times between required shut-downs of continuously operated process equipment and represents enormous practical and economic savings related to the specific stabilizer used.

| | TGA Data | | |
|---|---|---|---|
| | Isothermal at 280° C. Time (minutes) to Indicated Weight Loss of Stabilizer | Scanning (at 10° C.) per minute Temperature °C. to Indicated Weight Loss of Stabilizer | |
| | 50% | 10% | 50% |
| Stabilizer* | | | |
| A | 0.75 | 182 | 215 |
| B | 0.9  | 200 | 233 |
| C | 1.0  | 210 | 247 |
| D | 1.9  | 225 | 260 |
| E | 3.0  | 250 | 290 |
| F | 24   | 300 | 340 |
| G | 7.4  | 267 | 307 |
| of Example | | | |
| 6  | 180 | 338 | 384 |
| 15 | 420 | 350 | 390 |

*A is 2-(2-hydroxy-5-methylphenyl)-2H—benzotriazole.
B is 2-(2-hydroxy-3,5-di-tert-amylphenyl)-2H—benzotriazole.
C is 2-(2-hydroxy-3-tert-butyl-5-sec-butylphenyl)-2H—benzotriazole.
D is 2-(2-hydroxy-5-tert-octylphenyl)-2H—benzotriazole.
E is 2-[2-hydroxy-3-(1-phenylethyl)-5-methylphenyl]-2H—benzotriazole.
F is 2-[2-hydroxy-3,5-di-alpha,alpha-dimethylbenzyl)-phenyl]-2H—benzotriazole.
G is 2-[2-hydroxy-3-(alpha,alpha-dimethylbenzyl)-5-tert-octylphenyl]-2H—benzotriazole.

The benzotriazoles of Examples 6 and 15, are very much more resistant to thermogravimetric loss than the prior art benzotriazoles. This can be translated into enhanced resistance to sublimation and exudation (much less volatility) compared to the prior art benzotriazole.

The instant compounds incorporated in a stabilized polymer composition would remain there during processing permitting excellent processability coupled with a final polymer pellicle with greater protection against subsequent light-induced deterioration.

EXAMPLE 23

Absorbance at 340 nm

The compounds of this invention show unanticipated enhancement of absorbance at 340 nm as can be seen from a comparison of molar extinction coefficients E compared to state of the art compound F which lacks an alkyl substituent in the 5-position.

|  | Molar Extinction Coefficient E |
|---|---|
| Compound F | 15,100 |
| Compound of Example 6 | 18,200 |

EXAMPLE 24

A high solids thermosetting acrylic enamel consisting of 70 parts by weight of a copolymer prepared from methyl methacrylate, hydroxyethyl methacrylate, butyl acrylate and styrene and 30 parts by weight of hexakis methoxymethyl melamine as crosslinker and 0.1 parts by weight of p-toluene sulfonic acid is formulated with two (2) parts by weight of the following additives. The resulting clear enamel is then sprayed as clear coat onto steel panels precoated with silver metallic paint.

The panels after curing are then exposed outdoors in Florida for a period of 12 months. The retention of gloss is then determined:

| Stabilizer* | % Retention of Original Gloss |
|---|---|
| No Stabilizer | 24 |
| Stabilizer F | 86 |
| Stabilizer G | 83 |
| Compound of Example 6 | 82 |

*Stabilizers F and G are named in Example 22

What is claimed is:

1. A compound of the formula

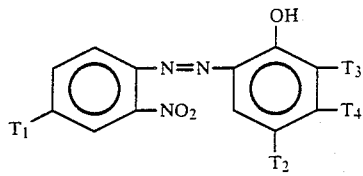

wherein
$T_1$ is alkyl of 8 to 18 carbon atoms, and
$T_2$ and $T_3$ are independently hydrogen, hydroxyl, alkyl of 8 to 18 carbon atoms or a group of formula II

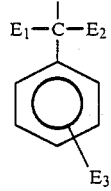

(II)

wherein $E_1$ and $E_2$ are independently hydrogen or alkyl of 1 to 4 carbon atoms and $E_3$ is hydrogen, halogen or alkyl of 1 to 4 carbon atoms,
$T_4$ is hydrogen or hydroxyl, with the proviso that $T_2$, $T_3$ add $T_4$ cannot each be hydrogen at the same time, and that only one of $T_2$, $T_3$ and $T_4$ can be hydroxyl at the same time.

2. The compound according to claim 1 which is 4-tert-octyl-2-nitro-2'-hydroxy-3',5'-di-(alpha,alpha-dimethylbenzyl)-azobenzene.

3. The compound according to claim 1 which is 4-n-dodecyl-2-nitro-2'-hydroxy-3',5'-di-(alpha,alpha-dimethylbenzyl)-azobenzene.

* * * * *